United States Patent [19]

Ghahramani

[11] 4,274,016
[45] Jun. 16, 1981

[54] VOLTAGE-TO-CURRENT CONVERTER

[75] Inventor: Iraj Ghahramani, Los Angeles, Calif.

[73] Assignee: International Telephone and Telegraph Corporation, New York, N.Y.

[21] Appl. No.: 10,021

[22] Filed: Feb. 7, 1979

[51] Int. Cl.³ .............................................. H03K 3/01
[52] U.S. Cl. .................................... 307/270; 307/261; 307/362; 330/105; 330/293
[58] Field of Search ............... 307/270, 350, 362, 261; 330/105, 260, 293

[56] References Cited

U.S. PATENT DOCUMENTS

| 3,602,829 | 8/1971 | Mansfield | 330/260 X |
| 3,878,374 | 4/1975 | Schlatter | 73/32 X |
| 3,902,111 | 8/1975 | Pfisterer, Jr. | 330/260 X |

Primary Examiner—John Zazworsky
Attorney, Agent, or Firm—A. Donald Stolzy

[57] ABSTRACT

A vibration densitometer having a magnetostrictive drive with a coil, and a crystal pick-up. A loop circuit including a driver amplifier provides the coil with current which leads the crystal voltage by 90 degrees for maximum efficiency. The driver amplifier is unusually small, inexpensive and accurate.

25 Claims, 4 Drawing Figures 19,274,016

1

VOLTAGE-TO-CURRENT CONVERTER

BACKGROUND OF THE INVENTION

This invention relates to voltage-to-current converters for, for example, vibration densitometers, and more particularly to an unusually small and inexpensive, yet accurate, current drive therefor.

In the past, densitometers have been large, expensive and inefficient because they have employed combination voltage and current drives of various phases.

PRIOR ART STATEMENT

Combination voltage and current drives of various phases are disclosed in U.S. Pat. No. 3,878,374 issued Apr. 15, 1975.

A permanent magnet biased 90 degree leading current drive is disclosed in copending application Ser. No. 837,454, filed Sept. 28, 1977, by P. Z. KALOTAY and I. GHAHRAMANI for DENSITOMETER.

Another current drive is disclosed in U.S. Pat. No. 4,151,743, issue on May 1, 1979 to I. Ghahramani for Densitometer Drive.

SUMMARY OF THE INVENTION

In accordance with the present invention, the above-described and other disadvantages of the prior art are overcome by providing a capacitor and inductor free driver amplifier feedback path to avoid phase shift and to effect a coil current directly proportional to the driver amplifier input voltage.

If desired, the 90 degree leading current drive may be adjusted earlier in the circuit.

BRIEF DESCRIPTION OF THE DRAWINGS

In the accompanying drawings which illustrate exemplary embodiments of the present invention.

DESCRIPTION OF THE PREFERRED EMBODIMENT

Figure 1:
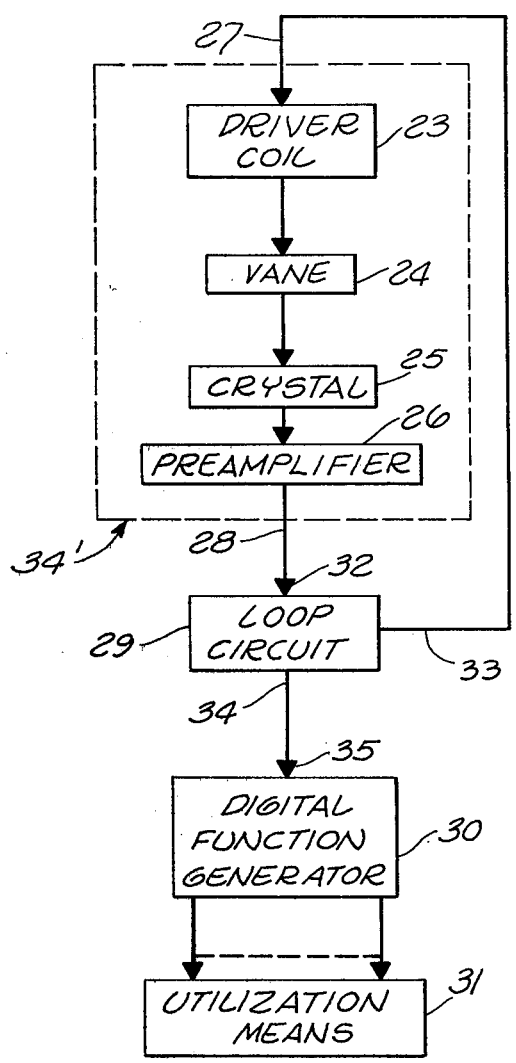
FIG. 1 is a block diagram of a vibration densitometer.

In the drawings, in FIG. 1, a vibration densitometer probe is indicated at 34' having a driver coil 23, a vane 24, a piezoelectric crystal 25 and a preamplifier 26.

Probe 34' has an input lead 27 and an output lead 28.

Other blocks shown in FIG. 1 are a loop circuit 29, a digital function generator 30 and utilization means 31. Loop circuit 29 has an input lead 32 connected from probe output lead 28, and output leads 33 and 34. Digital function generator 30 has an input lead 35 connected from loop circuit output lead 34. The output of digital function generator 30 is connected to utilization means 31.

The input lead 27 of probe 34' is connected from the output lead 33 of loop circuit 29. Probe 34' and loop circuit 29 form a closed loop electromechanical oscillator. Vane 24 is submerged in a fluid. The density of the fluid is a function of the frequency at which vane 24 vibrates.

Digital function generator 30 may have its input lead 35 connected from lead 33 or at other points in loop circuit 29. Loop circuit 29 impresses a square wave voltage on input lead 35 of digital function generator 30.

Utilization means 31 shown in FIG. 1 may be a density indicator, a specific gravity indicator, a process controller or otherwise.

The disclosure of the following patents are hereby incorporated herein:

(1) U.S. Pat. No. 3,677,067, issued July 18, 1972.
(2) U.S. Pat. No. 3,706,220, issued Dec. 19, 1972.
(3) U.S. Pat. No. 3,738,155, issued June 12, 1973.
(4) U.S. Pat. No. 3,741,000, issued June 26, 1973.
(5) U.S. Pat. No. 3,878,374, issued Apr. 15, 1975.

Probe 34' shown in FIG. 1 may be conventional. For example, it may or may not be identical to that disclosed in U.S. Pat. No. 3,878,374. Alternatively, probe 34' may be similar to or identical to a probe shown in any of the patents above cited.

Probe 34', digital function generator 30 and utilization means 31 may be similar to or identical to corresponding ones in said U.S. Pat. No. 3,878,374. Loop circuit 29 is not.

Figure 2:
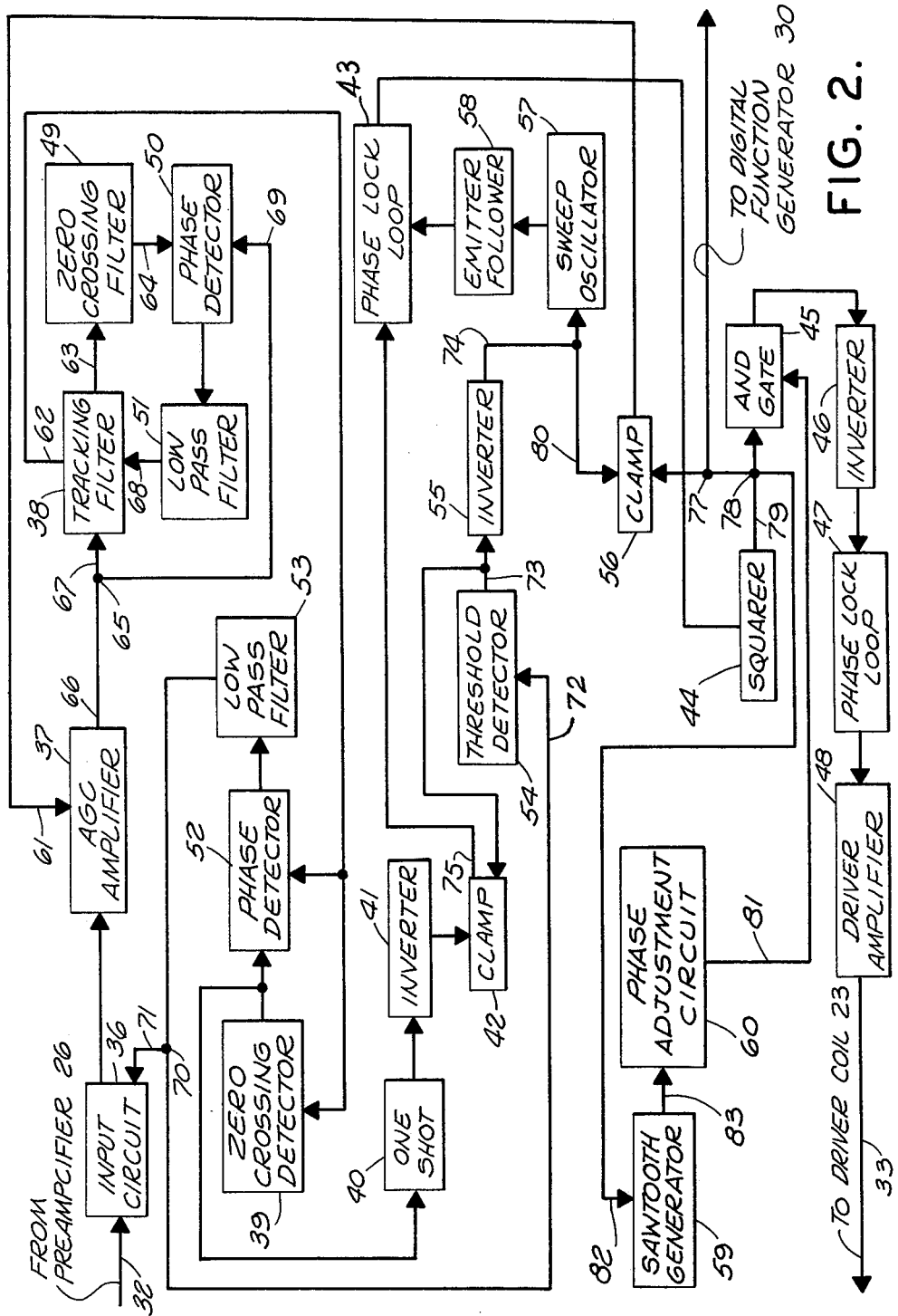
FIG. 2 is a detailed block diagram of a loop circuit shown in FIG. 1.

Loop circuit 29 is shown in FIG. 2 including an input circuit 36, an AGC amplifier 37, a tracking filter 38, a zero crossing detector 39, a one-shot multivibrator 40, an inverter 41, a clamp 42, a phase lock loop 43, a squarer 44, an AND gate 45, an inverter 46, a phase lock loop 47 and a driver amplifier 48 connected in succession as serial stages from input lead 32 of input circuit 36 to its output lead 33 and connected respectively from the output lead 28 of probe 34' and to the input lead 27 of probe 34'.

In FIG. 2, other stages are a zero crossing detector 49, a phase detector 50, a low pass filter 51, a phase detector 52, a low pass filter 53, a threshold detector 54, an inverter 55, a clamp 56, a sweep oscillator 57, an emitter-follower 58, a saw-tooth generator 59 and a phase adjustment circuit 60.

AGC amplifier 37 has an AGC input lead 61 connected from the output of clamp 56.

Tracking filter 38 has two output leads 62 and 63. Tracking filter output lead 63 is connected to the input of zero crossing detector 49. The output of zero crossing detector 49 is connected to one input 64 of phase detector 50. A junction is provided at 65 from which an output lead 66 of AGC amplifier 37 is connected. Tracking filter 38 has two input leads 67 and 68. Tracking filter input lead 67 is connected from junction 65.

Phase detector 50 has a second input lead 69 connected from junction 65. The output of phase detector 50 is connected to the input of low pass filter 51. The output of low pass filter 51 is connected to the input lead 68 of tracking filter 38.

The purpose of zero crossing detector 49, phase detector 50 and low pass filter 51 is to cause tracking filter 38 to track the frequency of output signal of AGC amplifier 37. The signal on the tracking filter input lead 68, thus, causes the passband thereof to straddle the frequency of the input to tracking filter 38 over input lead 67.

The output of tracking filter 38 on output lead 62 thereof is 90 degrees out of phase with the signal on the output lead 63 thereof. The signal from the tracking filter output lead is impressed upon zero crossing detector 39 and phase detector 52. The output of zero crossing detector 39 is impressed both upon phase detector 52 and one-shot 40. The output of phase detector 52 is impressed upon low pass filter 53.

A junction is provided at 70 connected from the output of low pass filter 53. A lead 71 is connected from junction 70 to input circuit 36 to the AGC input of an amplifier therein for automatic gain control.

Threshold detector 54 has an input 72 connected from junction 70. Input lead 72 of threshold detector 54, when below a predetermined potential, causes the potential of the output lead 73 of threshold detector 54 to go either high or low. The output lead 73 of threshold detector 54 is, thus, for example, either ground or +15 volts, as defined hereinafter. When the output of low pass filter 53 is below the predetermined potential, output lead 73 of threshold detector 54 is at ground.

Threshold detector 54 operates both of the clamps 42 and 56 and the sweep oscillator 57. Clamp 56 and sweep oscillator 57 are operated through the inverter 55.

Inverter 55 has an output lead 74 which also assumes potentials of +15 volts or ground.

Clamp 42 either passes the output of inverter 41 to the phase lock loop 43 or in the other state of the threshold detector 54, clamp 42 having an output lead 75, is operated to clamp the output lead 75 to ground. The output of inverter 55 is simply the reverse of the output detector 54. When the output of inverter 55 is high, sweep oscillator 57 receives power. When the output of inverter 55 is low, the output of sweep oscillator 57 is at ground.

Emitter follower 58 is connected between sweep oscillator 57 and phase lock loop 43. Phase lock loop 43 has an output lead 76 which is connected to squarer 44. Junctions are provided at 77 and 78. Squarer 44 has an output lead 79 connected to junction 78. Junction 78 is connected to junction 77. Clamp 56 is connected from junction 77 to AGC amplifier input lead 61.

When the output of threshold detector 54 is high, loop circuit 29 is tracking and opens clamp 42 to unground the output lead 75 thereof. Conversely, at the same time, inverter 55 grounds the input to sweep oscillator 57 and disables it. During tracking, inverter 55 also disables the output of clamp 56 by a connection 80 from inverter output lead 74 to clamp 56.

During searching, threshold detector 54 holds the output of clamp 42 at ground while inverter 55 operates sweep oscillator 57 and clamp 56 passes the output of squarer 44 to the AGC input lead 61 of AGC amplifier 37.

In FIG. 2, junction 77 is connected to digital function generator 30 shown in FIG. 1.

AND gate 45 receives an input from junction 78 and from an output lead 81 of phase adjustment circuit 60.

Saw-tooth generator 59 has an input lead 82 connected from junction 78, and an output lead 83 connected to an input of phase adjustment circuit 60.

Circuit 60 is manually adjustable to manually adjust the phase of the sine wave component of the current in coil 23 to be 90 degrees leading the output voltage of crystal 25. This adjustment makes the electromechanical oscillator oscillate with maximum efficiency.

OPERATION

In the embodiment of the invention shown in FIG. 1, probe 34' and loop circuit 29 provide an electromechanical oscillator which oscillates at a frequency dependent upon the density of the fluid in which vane 24 is immersed. The same is true of the pulse repetition frequency of the square wave voltage applied to the input lead 35 of digital function generator 30.

For more details of the operation, see U.S. Pat. No. 3,878,374.

Digital function generator 30 may be described as a digital linearization circuit. It produces a digital output directly proportional to density from the input signal thereto impressed upon the input lead 35 thereto.

All of the blocks shown in FIGS. 1 and 2 may be entirely conventional as disclosed in U.S. Pat. No. 3,878,374, except driver amplifier 48.

Figures 3, 4:
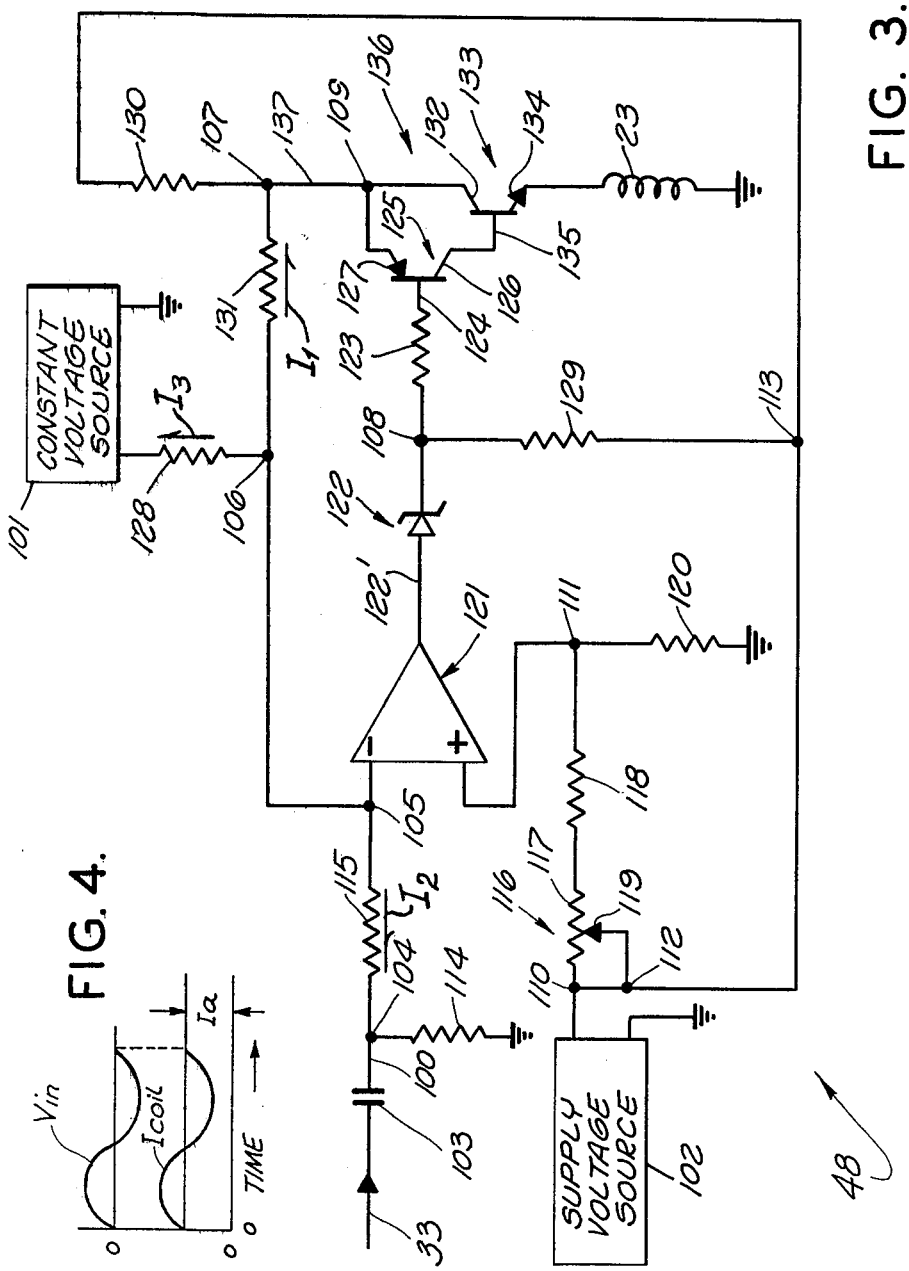
FIG. 3 is a schematic diagram of one embodiment of the driver amplifier of the present invention.
FIG. 4 is a graph of a group of waveforms characteristic of the operation of the present invention.

Driver amplifier 48 constructed in accordance with the present invention is shown in FIG. 3.

A current drive for coil 23, in phase with the input voltage of driver amplifier 48, is desired so as not to interfere with adjustment of circuit 60 and change the phase thereof for maximum efficiency. A current drive is also desirable because of the magnetostrictive driver in probe 34 which is controlled by the current and not the voltage across coil 23. See U.S. Pat. No. 3,677,067, for example.

Driver amplifier 48 is shown connected to driver coil 23 in FIG. 3. As will be shown, if $V_{in}$ is the voltage between lead 100 and ground, the current through coil 23, I coil, will be as shown in FIG. 4. The A.C. portion of Icoil is exactly in phase with $V_{in}$. Under certain conditions to be described, the average coil current $I_a$ (FIG. 4) may be defined as:

$$I_a = [V_{ref}]\left[\frac{R2}{RR_3}\right] \quad (i)$$

The terms of (1) will be defined hereinafter.

Preferably, because a magnetostrictive drive is used, I coil never goes negative. Hence, preferably $I_a$ is large enough to keep the current in coil 23 conventional from reversing direction. A magnetostrictive drive otherwise has a second harmonic component. See the said U.S. Pat. No. 3,677,067.

Preferably a conventional constant (regulated) voltage source 101 is provided in FIG. 3. However, the same may be adjustable and/or supplied from a zener diode (not shown). The magnitude of $I_a$ may be determined or adjusted by fixing the magnitude of the output voltage of source 101 relative to ground.

In FIG. 3, the coil current, under said conditions, may be made independent of the magnitude of the output voltage of a source 102 which thus need not be regulated.

In FIG. 3, conventional couplings, a capacitor 103 is connected between leads 33 and 100. Junctions are provided at 104, 105, 106, 107, 108, 109, 110, 111, 112 and 113. A resistor 114 is connected from junction 104 to ground, lead 100 being connected to junction 104. A resistor 115 is connected between junctions 104 and 105. Junctions 105 and 106 are connected together. Junctions 110 and 112 are connected together. Junction 110 is connected from source 102. A potentiometer 116 is provided having a winding 117 connected in series with a resistor 118 from junction 110 to junction 111. Potentiometer 116 has a wiper 119 connected from junction 112. A resistor 120 is connected from junction 111 to ground. A differential amplifier 121 is powered by soure 102 as its positive supply and ground as its negative supply. Amplifier 121 has an inverting input connected from junction 105, a noninverting input connected from junction 111, and an output connect through over a lead 122' through a zener diode 122 junction 108, a resistor 123 to the base 124 of a PNP transistor 125, transistor 125 having a collector 126 and an emitter 127. Emitter 127 is connected from junction 109.

A resistor 128 is connected from source 101 to junction 106. Junctions 112 and 113 are connected together. A resistor 129 is connected between junctions 108 and 113. A resistor 130 is connected between junctions 107 and 113. A resistor 131 is connected between junctions 106 and 107. Junctions 107 and 109 are connected together by a lead 137 and to the collector 132 (through junction 109) of an NPN transistor 133 having an emitter 134 connected to ground through coil 23, and a base 135 connected from collector 126.

Transistors 125 and 133 form all or a portion of a current control path 136. Most of the current in a lead 137 between junctions 107 and 109 flows through coil 23. As is well known, the percent current loss through base 124 is less than one hundred divided by the product of the B's of the transistor 125 and 133. This product is typically 100,000. The current loss is thus insignificant.

Typically, the gain of amplifier 121 is 100,000 or 500,000 or more. It is known that such a typical conventional high gain differential amplifier with a feedback circuit will drive its inverting input effectively to the same potential as that to its noninverting input. In other words, junction 105 is maintained effectively at the potential of junction 111. The input impedances of amplifier 121 are conventionally so high that they may be considered to be infinite or neglected.

With the foregoing knowledge and the following definitions, it is therefore possible to analyze the circuit of FIG. 3.

| Resistor | Resistance |
|---|---|
| 115 | $R_1$ |
| 131 | $R_2$ |
| 128 | $R_3$ |
| 130 | $R$ |
| 116 | $R_6$ |
| 118 | $R_5$ |
| 120 | $R_9$ |
| Source | Voltage |
| over lead 100 | $V_{in}$ |
| 101 | $V_{ref}$ |
| 102 | $V_s$ |
| Junction 107 | $V_{out}$ |

The current flowing in lead 137 is the current $I_R$ through resistor 130 less the leakage current through resistor 131. The current through lead 137 goes to coil 23, $$\text{where} \quad I_R = \frac{V_s - V_{out}}{R} \quad (2)$$

As stated previously, the voltage (with respect to ground) of junctions 105 and 111 is effectively the same. This voltage is $$K V_s \quad (3)$$

where $$K = \frac{R_9}{R_9 + R_5 + R_6} \quad (4)$$

See the voltage divider formed at junction 111 by potentiometer 116 and resistors 118 and 120 (from source 102). The current through resistors 115, 128 and 131 from junction 105 is then zero, thus:

$$\frac{V_{out} - KV_s}{R_2} + \frac{V_{in} - KV_s}{R_1} + \frac{V_{ref} - KV_s}{R_3} = 0 \quad (5)$$

Solving for $V_{out}$ $$V_{out} = KV_s - \left[\frac{V_{in} - KV_s}{R_1}\right][R_2] - \left[\frac{V_{ref} - KV_s}{R_3}\right][R_2] \quad (6)$$

Substituting $V_{out}$ in (6) for $V_{out}$ in (2) and eliminating factored terms:

$$I_R = \frac{V_s}{R} - \frac{KV_s}{R} + \frac{R_2 V_{in}}{RR_1} - \frac{KR_2 V_s}{RR_1} + \quad (6)$$

$$\frac{R_2 V_{ref}}{RR_3} - \frac{KR_2 V_s}{RR_3} \quad (7)$$

Factoring R and $V_s$ from the terms containing $V_s$:

$$I_R = \left[\frac{V_s}{R}\right]\left[1 - K\left(1 + \frac{R_2}{R_1} + \frac{R_2}{R_3}\right)\right] + \quad (8)$$

$$\frac{R_2 V_{in}}{RR_1} + \frac{R_2 V_{ref}}{RR_3}$$

Driver amplifier then may be made independent of $V_s$ by setting potentiometer wiper 119 to a position such that $$K = \frac{1}{1 + \frac{R_2}{R_1} + \frac{R_2}{R_3}} \quad (9)$$

In this case $$I_R = \frac{R_2 V_{in}}{RR_1} + \frac{R_2 V_{ref}}{RR_3}. \quad (10)$$

Thus, $I_R$ is in phase with $V_{in}$, and the rightmost term of (10) is $I_a$ of (1).

Some typical circuit values are as follows.

| Circuit Element | Value |
|---|---|
| Resistor 115 | 1.0 megohm |
| Resistor 128 | 1.0 megohm |
| Resistor 131 | 1.0 megohm |
| Resistor 114 | 10,000 ohms |
| Resistor 116 | 10,000 ohms set to 4,600 ohms (typ) |
| Resistor 118 | 100,000 ohms |
| Resistor 120 | 52,300 ohms |
| Resistor 129 | 3,300 ohms |
| Resistor 123 | 2,200 ohms |
| Resistor 130 | 30–60 ohms |
| Source 102 | 10–40 volts (30 typ.) |
| Source 101 | 6.2 volts (typ.) |
| $V_{out}$ At 107 | 6–7 volts |

The leakage current through resistor 131 is very small compared to that through resistor 130 because junctions 111 and 106 are effectively about $V_s/3$ or 10 volts and $V_{out}$ is about 2.0 volts peak-to-peak. Thus, even if R is 60 ohms, the current through resistor 131 is at most about 0.012 milliamperes and the current through resistor 130 is about 6.2/60×1000 or 103.3 milliamperes. Thus, effectively $I_R$ is equal to $I_{coil}$. Thus, $$I_{coil} = \frac{R_2 V_{in}}{RR_1} + \frac{R_2 V_{ref}}{RR_3} \quad (11)$$

This is true primarily because $R_2 >> R$, $V_{out}$ being of the same order of magnitude as $V_s/3$ and $V_s$.

Zener 122 and resistor 123 protect amplifier 121.

From the foregoing it will be appreciated that equation (9) may be rewritten $$\frac{R_9}{R_9 + R_5 + R_6} = \frac{1}{1 + \frac{R_2}{R_1} + \frac{R_2}{R_3}} \quad (12)$$

Solving for $R_6$ $$R_6 = R_2 R_9 \left[ \frac{1}{R_1} + \frac{1}{R_3} \right] - R_5$$

Equivalents may be used for components 102, 116, 118, 120, 122, 129, 123, 125 and 133. If the input signal is fairly pure A.C., in some cases 103 and 114 may be omitted. A field effect transistor or other device may be substituted for transistors 125 and 133. Transistors 125 and 133 may be different conductivity types or the same conductivity type. Either may be PNP or an NPN conductivity type. Resistor 114 provides a ground in the absence of signal.

In FIG. 3 it is one outstanding advantage that the opposite end of coil 23 can swing positive, for example, $V_s - 2$ volts and negative $-(V_s - 2)$ volts.

What is claimed is:

1. A voltage-to-current converter comprising a differential amplifier having an inverting input, a noninverting input and an output lead for carrying an output signal; an input voltage source having an output voltage including an A.C. component; an unregulated supply voltage source; a regulated supply voltage source; an output voltage junction; first means connected from said unregulated source to said non-inverting input to maintain it at an approximately predetermined potential; a first resistor connected from said input source to said inverting input; a second resistor connected from said regulated source to said inverting input; a feedback resistor connected from said output junction to said inverting input; a third resistor connected from said unregulated source to said output junction; an inductive winding having a grounded end and an end opposite said grounded end; a controllable current path between said output junction and said inductive winding opposite end; and second means connected from said differential amplifier output lead to control said current path in a manner to cause said inverting input to be driven effectively to the same potential as said noninverting input potential and to cause a current to flow in said inductive winding, said current having an A.C. component directly proportional to the A.C. component of the output voltage of said input voltage source.

2. The invention as defined in claim 1 wherein said inductive winding current has a D.C. component large enough such that the direction of said inductive winding current never reverses direction.

3. The invention as defined in claim 2, wherein said first means includes a variable resistor and a fourth resistor connected in series from said unregulated source to said noninverting input, a fifth resistor being connected from said noninverting input to ground, said variable resistor being adjusted until its resistance $R_6$ thereof is $$R_6 = R_2 R_9 \left[ \frac{1}{R_1} + \frac{1}{R_3} \right] - R_5$$

where
  $R_9$ is the resistance of said fifth resistor,
  $R_5$ is the resistance of said fourth resistor,
  $R_2$ is the resistance of said feedback resistor,
  $R_1$ is the resistance of said first resistor, and
  $R_3$ is the resistance of said second resistor.

4. The invention as defined in claim 3, wherein the effective inductive winding current $I_R$ is defined by $$I_R = \frac{R_2 V_{in}}{RR_1} + \frac{R_2 V_{ref}}{RR_3}$$

where
  $R$ is the resistance of said third resistor,
  $V_{in}$ is the output voltage of said input voltage source, and
  $V_{ref}$ is the output voltage of said regulated source.

5. The invention as defined in claim 4, wherein said controlled current path includes a PNP transistor and an NPN transistor, each of said transistors having a collector, an emitter and a base, said PNP transistor emitter and said NPN transistor collector being connected from said output junction, said NPN transistor emitter being connected to said inductive winding opposite end, and intermediate junction, a first auxiliary resistor connected from said intermediate junction to said unregulated source, a second auxiliary resistor connected from said PNP transistor base to said intermediate junction a zener diode connected from said differential amplifier output lead to said intermediate junction, said zener diode being poled to be back biased from said intermediate junction to said differential amplifier output lead.

6. The invention as defined in claim 1, wherein said first means includes a variable resistor and a fourth resistor connected in series from said unregulated source to said noninverting input, a fifth resistor being connected from said noninverting input to ground, said variable resistor being adjusted until its resistance $R_6$ thereof is $$R_6 = R_2 R_9 \left[ \frac{1}{R_1} + \frac{1}{R_3} \right] - R_5$$

where
  $R_9$ is the resistance of said fifth resistor,
  $R_5$ is the resistance of said fourth resistor,
  $R_2$ is the resistance of said feedback resistor,
  $R_1$ is the resistance of said first resistor, and
  $R_3$ is the resistance of said second resistor.

7. The invention as defined in claim 6, wherein the effective inductive winding current $I_R$ is defined by $$I_R = \frac{R_2 V_{in}}{RR_1} + \frac{R_2 V_{ref}}{RR_3}$$

where

R is the resistance of said third resistor, $V_{in}$ is the output voltage of said input voltage source, and $V_{ref}$ is the output voltage of said regulated source.

8. The invention as defined in claim 1, wherein said controlled current path includes a PNP transistor and an NPN transistor, each of said transistors having a collector, an emitter and a base, said PNP transistor emitter and said NPN transistor collector being connected from said output junction, said NPN transistor emitter being connected to said inductive winding opposite end, and intermediate junction, a first auxiliary resistor connected from said intermediate junction to said unregulated source, a second auxiliary resistor connected from said PNP transistor base to said intermediate junction a zener diode connected from said differential amplifier output lead to said intermediate junction, said zener diode being poled to be back biased from said intermediate junction to said differential amplifier output lead.

9. The invention as defined in claim 2, wherein said controlled current path includes a PNP transistor and an NPN transistor, each of said transistors having a collector, an emitter and a base, said PNP transistor emitter and said NPN transistor collector being connected from said output junction, said NPN transistor emitter being connected to said inductive winding opposite end, and intermediate junction, a first auxiliary resistor connected from said intermediate junction to said unregulated source, a second auxiliary resistor connected from said PNP transistor base to said intermediate junction a zener diode connected from said differential amplifier output lead to said intermediate junction, and zener diode being poled to be back biased from said intermediate junction to said differential amplifier output lead.

10. The invention as defined in claim 6, wherein said controlled current path includes a PNP transistor and an NPN transistor, each of said transistors having a collector, an emitter and a base, said PNP transistor emitter and said NPN transistor collector being connected from said output junction, said NPN transistor emitter being connected to said inductive winding opposite end, and intermediate junction, a first auxiliary resistor connected from said intermediate junction to said unregulated source, a second auxiliary resistor connected from said PNP transistor base to said intermediate junction a zener diode connected from said differential amplifier output lead to said intermediate junction, said zener diode being poled to be back biased from said intermediate junction to said differential amplifier output lead.

11. The invention as defined in claim 10 wherein the effective inductive winding current $I_R$ is defined by $$I_R = \frac{R_2 V_{in}}{RR_1} + \frac{R_2 V_{ref}}{RR_3}$$

where

R is the resistance of said third resistor, $V_{in}$ is the output voltage of said input voltage source, and $V_{ref}$ is the output voltage of said regulated source.

12. The invention as defined in claim 1, wherein said feedback resistor has a resistance $R_2$ and said third resistor has a resistance R, $R_2 >> R$ and the output voltages of all of said sources are of the same order of magnitude.

13. The invention as defined in claim 2, wherein said feedback resistor has a resistance $R_2$ and said third resistor has a resistance R, $R_2 >> R$ and the output voltages of all of said sources are of the same order of magnitude.

14. The invention as defined in claim 3, wherein said feedback resistor has a resistance $R_2$ and said third resistor has a resistance R, $R_2 >> R$ and the output voltages of all of said sources are of the same order of magnitude.

15. The invention as defined in claim 4, wherein said feedback resistor has a resistance $R_2$ and said third resistor has a resistance R, $R_2 >> R$ and the output voltages of all of said sources are of the same order of magnitude.

16. The invention as defined in claim 5, wherein said feedback resistor has a resistance $R_2$ and said third resistor has a resistance R, $R_2 >> R$ and the output voltages of all of said sources are of the same order of magnitude.

17. The invention as defined in claim 6, wherein said feedback resistor has a resistance $R_2$ and said third resistor has a resistance R, $R_2 >> R$ and the output voltages of all of said sources are of the same order of magnitude.

18. The invention as defined in claim 7, wherein said feedback resistor has a resistance $R_2$ and said third resistor has a resistance R, $R_2 >> R$ and the output voltages of all of said sources are of the same order of magnitude.

19. The invention as defined in claim 8, wherein said feedback resistor has a resistance $R_2$ and said third resistor has a resistance R, $R_2 >> R$ and the output voltages of all of said sources are of the same order of magnitude.

20. The invention as defined in claim 9, wherein said feedback resistor has a resistance $R_2$ and said third resistor has a resistance R, $R_2 >> R$ and the output voltages of all of said sources are of the same order of magnitude.

21. The invention as defined in claim 10, wherein said feedback resistor has a resistance $R_2$ and said third resistor has a resistance R, $$R_2 >> R$$

and the output voltages of all of said sources are of the same order of magnitude.

22. The invention as defined in claim 11, wherein said feedback resistor has a resistance $R_2$ and said third resistor has a resistance R, $$R_2 >> R$$

and the output voltages of all of said sources are of the same order of magnitude.

23. A voltage-to-current converter comprising: a differential amplifier having an inverting input, a non-inverting input and output lead for carrying an output signal; input means to supply input signals to said inverting input; an input voltage source having an output voltage; an unregulated supply voltage source; an output voltage junction; first means connected from said unregulated source to said non-inverting input to maintain it at an approximately predetermined potential; a first resistor connected from said input source to said inverting input; a feedback resistor connected from said output junction to said inverting input; a second resistor connected from said unregulated source to said output junction; a load having a grounded end and an end opposite said grounded end; a controllable current path between said output junction and said load opposite end; and second means connected from said differential amplifier output lead to control said current path in a manner to cause said inverting input to be driven effectively to the same potential as said non-inverting input potential and to cause a load current to flow through said load, said load current having at least a component directly proportional to the sum of the input signals to said inverting input.

24. The invention as defined in claim 23, wherein said controlled current path includes a PNP transistor and an NPN transistor, each of said transistors having a collector, an emitter and a base, said PNP transistor emitter and said NPN transistor collector being connected from said output junction, said NPN transistor emitter being connected to said inductive winding opposite end, and intermediate junction, a first auxiliary resistor connected from said intermediate junction to said unregulated source, a second auxiliary resistor connected from said PNP transistor base to said intermediate junction a zener diode connected from said differential amplifier output lead to said intermediate junction, said zener diode being poled to be back biased from said intermediate junction to said differential amplifier output lead.

25. The invention as defined in claim 23, wherein said feedback resistor has a resistance $R_2$ and said second resistor has a resistance R, $$R_2 >> R$$

and said input and unregulated supply voltage sources have respective output voltages of the same order of magnitude.

* * * * *